US012570983B2

(12) United States Patent
Thompson

(10) Patent No.: US 12,570,983 B2
(45) Date of Patent: **\*Mar. 10, 2026**

(54) COMPOSITION FOR REGULATING PRODUCTION OF INTERFERING RIBONUCLEIC ACID

(71) Applicant: Wyvern Pharmaceuticals Inc., Calgary (CA)

(72) Inventor: Bradley G. Thompson, Calgary (CA)

(73) Assignee: Wyvern Pharmaceuticals Inc., Calgary (CA)

( \* ) Notice: Subject to any disclaimer, the term of this patent is extended or adjusted under 35 U.S.C. 154(b) by 0 days.

This patent is subject to a terminal disclaimer.

(21) Appl. No.: 18/821,573

(22) Filed: Aug. 30, 2024

(65) Prior Publication Data

US 2026/0062707 A1 Mar. 5, 2026

(51) Int. Cl.
*C12N 15/113* (2010.01)
*C12N 15/86* (2006.01)
(52) U.S. Cl.
CPC .......... *C12N 15/1138* (2013.01); *C12N 15/86* (2013.01); *C12N 2310/141* (2013.01); *C12N 2750/14143* (2013.01)
(58) Field of Classification Search
CPC .......... C12N 15/1138; C12N 2310/141; C12N 15/86
See application file for complete search history.

(56) References Cited

U.S. PATENT DOCUMENTS

| | | | |
|---|---|---|---|
| 11,085,055 B2 | 8/2021 | Mallol et al. | |
| 11,162,102 B2 | 11/2021 | Minshull et al. | |
| 11,530,423 B1 | 12/2022 | Thompson | |
| 11,873,505 B2 | 1/2024 | Thompson | |
| 12,018,274 B2 | 6/2024 | Thompson | |
| 12,134,770 B1 | 11/2024 | Thompson | |
| 2024/0026377 A1 | 1/2024 | Thompson | |

FOREIGN PATENT DOCUMENTS

CA 2721333 A1 10/2009

OTHER PUBLICATIONS

Hughes and Nibbs, 2018, "A guide to chemokines and their receptors" The FEBS Journal, 285, p. 2944-2971 (Year: 2018).\*
O'Brien, et al., Aug. 3, 2018, "Overview of MicroRNA Biogenesis, Mechanisms of Actions, and Circulation" Front Endocrinol (Lausanne), 9:402, p. 1-12 (Year: 2018).\*
Lu et al., Oct. 29, 2013, "miR-9 targets CXCR4 and functions as a potential tumor suppressor in nasopharyngeal carcinoma" Carcinogenesis, p. 554-563 (Year: 2013).\*
Ren et al., 2020, "MiR-140-3p Ameliorates the Progression of Osteoarthritis via Targeting CXCR4" Biol. Pharm. Bull., 43, p. 810-816 (Year: 2020).\*

Agarwal et al., 2015, "Predicting effective microRNA target sites in mammalian mRNAs" eLife, 4: e05005 (Year: 2015).\*
*Homo sapiens* C-X-C motif chemokine receptor 4 (CXCR4), RefSeqGene (LRG_51) on chromosome 2, NCBI Reference Sequence: NG_011587.1 (Year: 2021).\*
*Homo sapiens* C-X-C motif chemokine receptor 4 (CXCR4), transcript variant 1, mRNA, NCBI Reference Sequence: NM_001008540.2 (Year: 2024).\*
*Homo sapiens* C-X-C motif chemokine receptor 4 (CXCR4), transcript variant 3, mRNA, NCBI Reference Sequence: NM_001348056.2 (Year: 2024).\*
*Homo sapiens* C-X-C motif chemokine receptor 4 (CXCR4), transcript variant 5, mRNA, NCBI Reference Sequence: NM_001348060.2 (Year: 2024).\*
*Homo sapiens* G protein-coupled receptor 35 (GPR35), transcript variant 1, mRNA, NCBI Reference Sequence: NM_005301.5 ( Year: 2023).\*
*Homo sapiens* C-X-C motif chemokine receptor 6 (CXCR6), transcript variant 1, mRNA, NCBI Reference Sequence: NM_006564.2 (Year: 2023).\*
Momin et al., 2021, Cells, 10, 3097, p. 1-21 (Year: 2021).\*
Bottoni et al. "Targeting BTK through microRNA in chronic lymphocytic leukemia." Blood, The Journal of the American Society of Hematology 128.26 (2016): 3101-3112.
Brutons Tyrosine Kinase Genbank Sequence (2023).
Christensen et al. "Recombinant adeno-associated virus-mediated microRNA delivery into the postnatal mouse brain reveals a role for miR-134 in dendritogenesis in vivo." Frontiers in neural circuits 3 (2010): 848.
Bofill-De Ros et al. "Guidelines for the optimal design of miRNA-based shRNAs." Methods 103 (2016): 157-166.
Van den Berg, et al., pp. 1-12, Molecular Therapy—Nucleic Acids, vol. 5, 2016 (Year: 2016).
Nature (2010. Gene Expression. Scitable. Available online at Nature. com) <https://www.nature.com/scitable/topicpage/gene-expression-14121669> (2010).
GenBank EGF Sequence (2023).
Ahmadzadeh et al. "BRAF mutation in hairy cell leukemia." Oncology reviews 8.2 (2014): 253.

(Continued)

*Primary Examiner* — Jennifer Dunston
*Assistant Examiner* — Jenna L Persons
(74) *Attorney, Agent, or Firm* — Gowling WLG (Canada) LLP

(57) ABSTRACT

The embodiments of the present disclosure relate to one or more compositions or methods that upregulate the production of one or more sequences of micro-interfering ribonucleic acid (miRNA). The sequences of miRNA may be complimentary to a sequence of target messenger RNA (mRNA) that encodes for translation of a target biomolecule, such as CXCR4. The miRNA can cause the target mRNA to be degraded or inactivated, thereby causing a decrease in bioavailability of the target biomolecule because it is degraded or inactivated by the miRNA. Decreasing the bioavailability of the target biomolecule within a subject that is administered the one or more compositions may address the afflictions experienced by the subject due to expression of the target biomolecule.

2 Claims, No Drawings

Specification includes a Sequence Listing.

(56)                    References Cited

OTHER PUBLICATIONS

Patton et al. "Biogenesis, delivery, and function of extracellular RNA." Journal of extracellular vesicles 4.1 (2015): 27494.

Clark et al. "Detection of BRAF splicing variants in plasma-derived cell-free nucleic acids and extracellular vesicles of melanoma patients failing targeted therapy therapies." Oncotarget 11.44 (2020): 4016.

NCBI search results for SEQ ID No. 5 (2024).

NCBI Nucleotide Sequence ALK Lingand, search performed Dec. 26, 2024 (2023).

NCBI Nucleotide Sequence ALK Receptor, search performed Dec. 26, 2024 (2023).

GenBank EGFR Sequence (2023).

Genbank FLT3 Sequence (2024).

NCBI Nucleotide Sequence for PARP, search performed Dec. 26, 2024 (2024).

Tritschler et al. "Concepts and limitations for learning developmental trajectories from single cell genomics." Development 146.12 (2019): dev170506.

Kondratov et al. "Direct head-to-head evaluation of recombinant adeno-associated viral vectors manufactured in human versus insect cells." Molecular Therapy 25.12 (2017): 2661-2675.

Wang et al. "Adeno-associated virus vector as a platform for gene therapy delivery". Nat Rev Drug Discov. May 2019;18(5):358-378. (Year: 2019).

Gorski, S., Vogel, J. & Doudna, J. RNA-based recognition and targeting: sowing the seeds of specificity. Nat Rev Mol Cell Biol 18, 215-228 (2017). (Year: 2017).

Denzler R et al. Impact of MicroRNA Levels, Target-Site Complementarity, and Cooperativity on Competing Endogenous RNA-Regulated Gene Expression. Mol Cell. Nov. 3, 2016;64(3):565-579. doi: 10.1016/j.molcel.2016.09.027 (Year: 2016).

* cited by examiner

COMPOSITION FOR REGULATING PRODUCTION OF INTERFERING RIBONUCLEIC ACID

This application contains a Sequence Listing electronically submitted via Patent Center to the United States Patent and Trademark Office as an XML Document file entitled "A8149692US-SequenceListing.xml" created on 2024 Aug. 29 and having a size of 15,915 bytes. The information contained in the Sequence Listing is incorporated by reference herein.

TECHNICAL FIELD

The present disclosure generally relates to compositions for regulating production of micro-interfering ribonucleic acid (miRNA). In particular, the present disclosure relates to compositions for regulating gene expression and therefore, the production of miRNA that will suppress CXCR4 expression.

BACKGROUND

Bioactive molecules, including receptors, are necessary for the homeostatic control of biological systems.

When bioactive molecules are over-expressed or mis-expressed, homeostasis is lost, and disease is often the result.

As such, it may be desirable to establish therapies, treatments and/or interventions that address when homeostasis and regulation of bioactive molecules is lost to prevent or treat the resulting disease.

SUMMARY

Some embodiments of the present disclosure relate to one or more compositions that upregulate the production of one or more sequences of micro-interfering ribonucleic acid (miRNA). The sequences of miRNA may be complimentary to a sequence of target messenger RNA (mRNA) that encodes for translation of a target biomolecule and the miRNA can cause the target mRNA to be degraded or inactivated, thereby causing a decrease in bioavailability of the target biomolecule because it is degraded or inactivated by the miRNA, thereby decreasing the bioavailability of the target biomolecule within a subject that is administered the one or more compositions. In some embodiments of the present disclosure, the target biomolecule is a C-X-C motif chemokine receptor molecule such as CXCR4. In some embodiments of the present disclosure, the target biomolecule participates, directly or indirectly, in one or more immune responses. For example, the target biomolecule may be a chemokine receptor molecule that is a protein, a protein-protein complex-such as a receptor ligand pair- or other type of biomolecule that directly or indirectly suppresses an immune response or that directly or indirectly stimulates an immune response.

In some embodiments of the present disclosure the compositions comprise a plasmid of deoxyribonucleic acid (DNA) that includes one or more insert sequences of nucleotides that encode for the production of miRNA and a backbone sequence of nucleic acids that facilitates introduction of the one or more insert sequences into one or more of a subject's cells where it is expressed and/or replicated. Expression of the one or more insert sequences by one or more cells of the subject results in an increased production of the miRNA and, therefore, decreased translation or production of the target biomolecule by one or more of the subject's cells.

Some embodiments of the present disclosure relate to compositions that upregulate the production of miRNA that degrades, or causes degradation of, or inactivates or causes the inactivation of, the target mRNA of the target biomolecule.

Some embodiments of the present disclosure relate to a recombinant plasmid. In some embodiments of the present disclosure, the RP comprises a nucleotide sequence of SEQ ID NO. 1 and SEQ ID NO. 2. The RP comprises a nucleotide sequence encoding one or more nucleotide sequences encoding a miRNA sequence that targets mRNA of CXCR4.

Some embodiments of the present disclosure relate to a method of making a composition/target cell complex. The method comprising a step of administering a RP comprising SEQ ID NO. 1 and SEQ ID NO. 2 to a target cell for forming the composition/target cell complex, wherein the composition/target cell complex causes the target cell to increase production of one or more sequences of miRNA that decreases production of a target biomolecule.

Embodiments of the present disclosure relate to at least one approach for inducing endogenous production of one or more sequences of miRNA that target and silence mRNA of a target biomolecule, for example CXCR4. A first approach utilizes gene vectors containing nucleotide sequences for increasing the endogenous production of one or more sequences of miRNA, which are complete or partial sequences and/or combinations thereof, that target and silence the mRNA of CXCR4, which can be administered to a subject to increase the subject's production of one or more sequences of the miRNA.

DETAILED DESCRIPTION

Unless defined otherwise, all technical and scientific terms used therein have the meanings that would be commonly understood by one of skill in the art in the context of the present description. Although any methods and materials similar or equivalent to those described therein can also be used in the practice or testing of the present disclosure, the preferred methods and materials are now described. All publications mentioned therein are incorporated therein by reference to disclose and describe the methods and/or materials in connection with which the publications are cited.

As used therein, the singular forms "a", "an", and "the" include plural references unless the context clearly dictates otherwise. For example, reference to "a composition" includes one or more compositions and reference to "a subject" or "the subject" includes one or more subjects.

As used therein, the terms "about" or "approximately" refer to within about 25%, preferably within about 20%, preferably within about 15%, preferably within about 10%, preferably within about 5% of a given value or range. It is understood that such a variation is always included in any given value provided therein, whether or not it is specifically referred to.

As used therein, the term "ameliorate" refers to improve and/or to make better and/or to make more satisfactory.

As used therein, the term "cell" refers to a single cell as well as a plurality of cells or a population of the same cell type or different cell types. Administering a composition to a cell includes in vivo, in vitro and ex vivo administrations and/or combinations thereof.

As used therein, the term "complex" refers to an association, either direct or indirect, between one or more particles of a composition and one or more target cells. This association results in a change in the metabolism of the target cell. As used therein, the phrase "change in metabolism" refers to an increase or a decrease in the one or more target cells' production of one or more proteins, and/or any post-translational modifications of one or more proteins.

As used therein, the term "composition" refers to a substance that, when administered to a subject, causes one or more chemical reactions and/or one or more physical reactions and/or one or more physiological reactions and/or one or more immunological reactions in the subject. In some embodiments of the present disclosure, the composition is a plasmid vector.

As used therein, the term "endogenous" refers to the production and/or modification of a molecule that originates within a subject.

As used therein, the term "exogenous" refers to a molecule that is within a subject but that did not originate within the subject. As used therein, the terms "production", "producing" and "produce" refer to the synthesis and/or replication of DNA, the transcription of one or more sequences of RNA, the translation of one or more amino acid sequences, the post-translational modifications of an amino acid sequence, and/or the production of one or more regulatory molecules that can influence the production and/or functionality of an effector molecule or an effector cell. For clarity, "production" is also used therein to refer to the functionality of a regulatory molecule, unless the context reasonably indicates otherwise.

As used therein, the term "subject" refers to any therapeutic target that receives the composition. The subject can be a vertebrate, for example, a mammal including a human. The term "subject" does not denote a particular age or sex. The term "subject" also refers to one or more cells of an organism, an in vitro culture of one or more tissue types, an in vitro culture of one or more cell types, ex vivo preparations, and/or a sample of biological materials such as tissue, and/or biological fluids.

As used therein, the term "target biomolecule" refers to a C-X-C motif chemokine receptor that is found within a subject. A biomolecule may be endogenous or exogenous to a subject and when bioavailable the biomolecule may suppress, influence or stimulate an immune process within the subject.

As used therein, the term "target cell" refers to one or more cells and/or cell types that are deleteriously affected, either directly or indirectly, by a dysregulated biomolecule. The term "target cell" also refers to cells that are not deleteriously affected but that are the cells in which it is desired that the composition interacts.

As used therein, the term "therapeutically effective amount" refers to the amount of the composition used that is of sufficient quantity to ameliorate, treat and/or inhibit one or more of a disease, disorder or a symptom thereof. The "therapeutically effective amount" will vary depending on the composition used, the route of administration of the composition and the severity of the disease, disorder or symptom thereof. The subject's age, weight and genetic make-up may also influence the amount of the composition that will be a therapeutically effective amount.

As used therein, the terms "treat", "treatment" and "treating" refer to obtaining a desired pharmacologic and/or physiologic effect. The effect may be prophylactic in terms of completely or partially preventing an occurrence of a disease, disorder or symptom thereof and/or the effect may be therapeutic in providing a partial or complete amelioration or inhibition of a disease, disorder, or symptom thereof.

Additionally, the term "treatment" refers to any treatment of a disease, disorder, or symptom thereof in a subject and includes: (a) preventing the disease from occurring in a subject which may be predisposed to the disease but has not yet been diagnosed as having it; (b) inhibiting the disease, i.e., arresting its development; and (c) ameliorating the disease.

As used therein, the terms "unit dosage form" and "unit dose" refer to a physically discrete unit that is suitable as a unitary dose for patients. Each unit contains a predetermined quantity of the composition and optionally, one or more suitable pharmaceutically acceptable carriers, one or more excipients, one or more additional active ingredients, or combinations thereof. The amount of composition within each unit is a therapeutically effective amount.

Where a range of values is provided therein, it is understood that each intervening value, to the tenth of the unit of the lower limit unless the context clearly dictates otherwise, between the upper and lower limit of that range and any other stated or intervening value in that stated range, is encompassed within the disclosure. The upper and lower limits of these smaller ranges may independently be included in the smaller ranges, and are also, encompassed within the disclosure, subject to any specifically excluded limit in the stated range. Where the stated range includes one or both of the limits, ranges excluding either or both of those included limits are also included in the disclosure.

In some embodiments of the present disclosure, a composition is a recombinant plasmid (RP) for introducing genetic material, such as one or more nucleotide sequences, into a target cell for reproduction or transcription of an insert that comprises one or more nucleotide sequences that are carried within the RP. In some embodiments of the present disclosure, the RP is delivered without a carrier, by a viral vector, by a protein coat, or by a lipid vesicle. In some embodiments of the present disclosure, the vector is an adeno-associated virus vector.

In some embodiments of the present disclosure, the insert comprises one or more nucleotide sequences that encode for production of at least one sequence of miRNA that decreases the production of target biomolecules. The miRNA may, directly or indirectly, bind to and degrade the target mRNA or otherwise inactivate the target mRNA so that less or none of the target-biomolecule protein is produced.

In some embodiments of the present disclosure, the target biomolecule is CXCR4.

In some embodiments of the present disclosure, the insert comprises one or more nucleotide sequences that each encode one or more miRNA sequences that may be complimentary to and degrade, or cause degradation of, mRNA of the target biomolecule.

Some embodiments of the present disclosure relate to a composition that can be administered to a subject with a condition that results, directly or indirectly, from the production of a dysregulated biomolecule. When a therapeutically effective amount of the composition is administered to the subject, the subject may change production and/or functionality of one or more biomolecules.

In some embodiments of the present disclosure, the subject may respond to receiving the therapeutic amount of the composition by changing production and/or functionality of one or more intermediary molecules by changing production of one or more DNA sequences, one or more RNA sequences, and/or one or more proteins that regulate the levels and/or functionality of the one or more intermediary molecules. The one or more intermediary molecules regulate the subject's levels and/or functionality of the one or more biomolecules.

In some embodiments of the present disclosure, administering a therapeutic amount of the composition to a subject upregulates the production, functionality or both one or more sequences of miRNA that each target the mRNA of one or more target biomolecules. In some embodiments of the present disclosure, there are one, two, three, four, five, or six miRNA sequences that each are complimentary to and degrade, or cause degradation of, one biomolecule, such as CXCR4. In some embodiments of the present disclosure, the composition may comprise multiple copies of the same nucleotide sequence of miRNA.

In some embodiments of the present disclosure, the composition is an RP that may be used for gene therapy. The gene therapy is useful for increasing the subject's endogenous production of one or more sequences of miRNA that target the mRNA of a target biomolecule. For example, the RP can contain one or more nucleotide sequences that cause increased production of one or more nucleotide sequences that cause an increased production of one or more miRNA sequences that are each complimentary to and degrade, or cause degradation of, or inactivate, or cause inactivation of, one biomolecule, such as CXCR4.

In some embodiments of the present disclosure, the delivery vehicle of the RP used for gene therapy may be a virus that can be enveloped, or not (unenveloped), replication effective or not (replication ineffective), or combinations thereof. In some embodiments of the present disclosure, the vector is a virus that is not enveloped and not replication effective. In some embodiments of the present disclosure, the vector is a virus of the Parvoviridae family. In some embodiments of the present disclosure, the vector is a virus of the genus Dependoparvovirus. In some embodiments of the present disclosure, the vector is an adeno-associated virus (AAV). In some embodiments of the present disclosure, the vector is a recombinant AAV. In some embodiments of the present disclosure, the vector is a recombinant AAV6.2FF.

In some embodiments of the present disclosure, the delivery vehicle of the RP used for gene therapy may be a protein coat.

In some embodiments of the present disclosure, the delivery vehicle of the RP used for gene therapy may be a lipid vesicle.

The embodiments of the present disclosure also relate to administering a therapeutically effective amount of the composition. In some embodiments of the present disclosure, the therapeutically effective amount of the composition that is administered to a patient is between about 10 and about $1 \times 10^{16}$ $TCID_{50}$/kg (50% tissue culture infective dose per kilogram of the patient's body mass. In some embodiments of the present disclosure, the therapeutically effective amount of the composition that is administered to the patient is about $1 \times 10^{13}$ $TCID_{50}$/kg. In some embodiments of the present disclosure, the therapeutically effective amount of the composition that is administered to a patient is measured in TPC/kg (total particle count of the composition per kilogram of the patient's body mass). In some embodiments the therapeutically effective amount of the composition is between about 10 and about $1 \times 10^{16}$ TCP/kg.

Some embodiments of the present disclosure relate to an adenovirus associated virus (AAV) genome consisting of a RP that when operable inside a target cell will cause the target cell to produce a miRNA sequence that downregulates production of a biomolecule, with an example being CXCR4. The RP is comprised of AAV2 inverted terminal repeats (ITRs), a composite CASI promoter, a human growth hormone (HGH) signal peptide followed by a miRNA expression cassette containing up to six different miRNAs targeting CXCR4, followed by a Woodchuck Hepatitis Virus post-transcriptional regulatory element (WPRE) and an SV40 polyA signal.

SEQ ID NO. 1 (backbone sequence No. 1):
5' TCTAGAATAATCAACCTCTGGATTACAAAATTTGTGAAAGATTGACT

GGTATTCTTAACTATGTTGCTCCTTTTACGCTATGTGGATACGCTGCTTT

AATGCCTTTGTATCATGCTATTGCTTCCCGTATGGCTTTCATTTTCTCCT

CCTTGTATAAATCCTGGTTGCTGTCTCTTTATGAGGAGTTGTGGCCCGTT

GTCAGGCAACGTGGCGTGGTGTGCACTGTGTTTGCTGACGCAACCCCCAC

TGGTTGGGGCATTGCCACCACCTGTCAGCTCCTTTCCGGGACTTTCGCTT

TCCCCCTCCCTATTGCCACGGCGGAACTCATCGCCGCCTGCCTTGCCCGC

TGCTGGACAGGGGCTCGGCTGTTGGGCACTGACAATTCCGTGGTGTTGTC

GGGGAAATCATCGTCCTTTCCTTGGCTGCTCGCCTGTGTTGCCACCTGGA

TTCTGCGCGGGACGTCCTTCTGCTACGTCCCTTCGGCCCTCAATCCAGCG

GACCTTCCTTCCCGCGGCCTGCTGCCGGCTCTGCGGCCTCTTCCGCGTCT

TCGCCTTCGCCCTCAGACGAGTCGGATCTCCCTTTGGGCCGCCTCCCCGC

CTAAGCTTATCGATACCGTCGAGATCTAACTTGTTTATTGCAGCTTATAA

TGGTTACAAATAAAGCAATAGCATCACAAATTTCACAAATAAAGCATTTT

TTTCACTGCATTCTAGTTGTGGTTTGTCCAAACTCATCAATGTATCTTAT

CATGTCTGGATCTCGACCTCGACTAGAGCATGGCTACGTAGATAAGTAGC

ATGGCGGGTTAATCATTAACTACAAGGAACCCCTAGTGATGGAGTTGGCC

ACTCCCTCTCTGCGCGCTCGCTCGCTCACTGAGGCCGGGCGACCAAAGGT

CGCCCGACGCCCGGGCTTTGCCCGGGCGGCCTCAGTGAGCGAGCGAGCGC

GCAGCTGGCGTAATAGCGAAGAGGCCCGCACCGATCGCCCTTCCCAACAG

TTGCGCAGCCTGAATGGCGAATGGCGATTCCGTTGCAATGGCTGGCGGTA

ATATTGTTCTGGATATTACCAGCAAGGCCGATAGTTTGAGTTCTTCTACT

CAGGCAAGTGATGTTATTACTAATCAAAGAAGTATTGCGACAACGGTTAA

TTTGCGTGATGGACAGACTCTTTTACTCGGTGGCCTCACTGATTATAAAA

ACACTTCTCAGGATTCTGGCGTACCGTTCCTGTCTAAAATCCCTTTAATC

GGCCTCCTGTTTAGCTCCCGCTCTGATTCTAACGAGGAAAGCACGTTATA

CGTGCTCGTCAAAGCAACCATAGTACGCGCCCTGTAGCGGCGCATTAAGC

GCGGCGGGTGTGGTGGTTACGCGCAGCGTGACCGCTACACTTGCCAGCGC

CCTAGCGCCCGCTCCTTTCGCTTTCTTCCCTTCCTTTCTCGCCACGTTCG

CCGGCTTTCCCCGTCAAGCTCTAAATCGGGGGCTCCCTTTAGGGTTCCGA

TTTAGTGCTTTACGGCACCTCGACCCCAAAAAACTTGATTAGGGTGATGG

TTCACGTAGTGGGCCATCGCCCTGATAGACGGTTTTTCGCCCTTTGACGT

TGGAGTCCACGTTCTTTAATAGTGGACTCTTGTTCCAAACTGGAACAACA

CTCAACCCTATCTCGGTCTATTCTTTTGATTTATAAGGGATTTTGCCGAT

TTCGGCCTATTGGTTAAAAAATGAGCTGATTTAACAAAAATTTAACGCGA

-continued

ATTTTAACAAAATATTAACGTTTACAATTTAAATATTTGCTTATACAATC

TTCCTGTTTTTGGGGCTTTTCTGATTATCAACCGGGGTACATATGATTGA

CATGCTAGTTTTACGATTACCGTTCATCGATTCTCTTGTTTGCTCCAGAC

TCTCAGGCAATGACCTGATAGCCTTTGTAGAGACCTCTCAAAAATAGCTA

CCCTCTCCGGCATGAATTTATCAGCTAGAACGGTTGAATATCATATTGAT

GGTGATTTGACTGTCTCCGGCCTTTCTCACCCGTTTGAATCTTTACCTAC

ACATTACTCAGGCATTGCATTTAAAATATATGAGGGTTCTAAAAATTTTT

ATCCTTGCGTTGAAATAAAGGCTTCTCCCGCAAAAGTATTACAGGGTCAT

AATGTTTTTGGTACAACCGATTTAGCTTTATGCTCTGAGGCTTTATTGCT

TAATTTTGCTAATTCTTTGCCTTGCCTGTATGATTTATTGGATGTTGGAA

TTCCTGATGCGGTATTTTCTCCTTACGCATCTGTGCGGTATTTCACACCG

CATATGGTGCACTCTCAGTACAATCTGCTCTGATGCCGCATAGTTAAGCC

AGCCCCGACACCCGCCAACACCCGCTGACGCGCCCTGACGGGCTTGTCTG

CTCCCGGCATCCGCTTACAGACAAGCTGTGACCGTCTCCGGGAGCTGCAT

GTGTCAGAGGTTTTCACCGTCATCACCGAAACGCGCGAGACGAAAGGGCC

TCGTGATACGCCTATTTTTATAGGTTAATGTCATGATAATAATGGTTTCT

TAGACGTCAGGTGGCACTTTTCGGGGAAATGTGCGCGGAACCCCTATTTG

TTTATTTTTCTAAATACATTCAAATATGTATCCGCTCATGAGACAATAAC

CCTGATAAATGCTTCAATAATATTGAAAAAGGAAGAGTATGAGTATTCAA

CATTTCCGTGTCGCCCTTATTCCCTTTTTTGCGGCATTTTGCCTTCCTGT

TTTTGCTCACCCAGAAACGCTGGTGAAAGTAAAAGATGCTGAAGATCAGT

TGGGTGCACGAGTGGGTTACATCGAACTGGATCTCAACAGCGGTAAGATC

CTTGAGAGTTTTCGCCCCGAAGAACGTTTTCCAATGATGAGCACTTTTAA

AGTTCTGCTATGTGGCGCGGTATTATCCCGTATTGACGCCGGGCAAGAGC

AACTCGGTCGCCGCATACACTATTCTCAGAATGACTTGGTTGAGTACTCA

CCAGTCACAGAAAAGCATCTTACGGATGGCATGACAGTAAGAGAATTATG

CAGTGCTGCCATAACCATGAGTGATAACACTGCGGCCAACTTACTTCTGA

CAACGATCGGAGGACCGAAGGAGCTAACCGCTTTTTTGCACAACATGGGG

GATCATGTAACTCGCCTTGATCGTTGGGAACCGGAGCTGAATGAAGCCAT

ACCAAACGACGAGCGTGACACCACGATGCCTGTAGCAATGGCAACAACGT

TGCGCAAACTATTAACTGGCGAACTACTTACTCTAGCTTCCCGGCAACAA

TTAATAGACTGGATGGAGGCGGATAAAGTTGCAGGACCACTTCTGCGCTC

GGCCCTTCCGGCTGGCTGGTTTATTGCTGATAAATCTGGAGCCGGTGAGC

GTGGGTCTCGCGGTATCATTGCAGCACTGGGGCCAGATGGTAAGCCCTCC

CGTATCGTAGTTATCTACACGACGGGGAGTCAGGCAACTATGGATGAACG

AAATAGACAGATCGCTGAGATAGGTGCCTCACTGATTAAGCATTGGTAAC

TGTCAGACCAAGTTTACTCATATATACTTTAGATTGATTTAAAACTTCAT

TTTTAATTTAAAAGGATCTAGGTGAAGATCCTTTTTTGATAATCTCATGAC

CAAAATCCCTTAACGTGAGTTTTCGTTCCACTGAGCGTCAGACCCCGTAG

AAAAGATCAAAGGATCTTCTTGAGATCCTTTTTTTCTGCGCGTAATCTGC

TGCTTGCAAACAAAAAAACCACCGCTACCAGCGGTGGTTTGTTTGCCGGA

-continued

TCAAGAGCTACCAACTCTTTTTCCGAAGGTAACTGGCTTCAGCAGAGCGC

AGATACCAAATACTGTCCTTCTAGTGTAGCCGTAGTTAGGCCACCACTTC

AAGAACTCTGTAGCACCGCCTACATACCTCGCTCTGCTAATCCTGTTACC

AGTGGCTGCTGCCAGTGGCGATAAGTCGTGTCTTACCGGGTTGGACTCAA

GACGATAGTTACCGGATAAGGCGCAGCGGTCGGGCTGAACGGGGGGGTTCG

TGCACACAGCCCAGCTTGGAGCGAACGACCTACACCGAACTGAGATACCT

ACAGCGTGAGCTATGAGAAAGCGCCACGCTTCCCGAAGGGAGAAAGGCGG

ACAGGTATCCGGTAAGCGGCAGGGTCGGAACAGGAGAGCGCACGAGGGAG

CTTCCAGGGGGAAACGCCTGGTATCTTTATAGTCCTGTCGGGTTTCGCCA

CCTCTGACTTGAGCGTCGATTTTTGTGATGCTCGTCAGGGGGGCGGAGCC

TATGGAAAAACGCCAGCAACGCGGCCTTTTTACGGTTCCTGGCCTTTTGC

TGGCCTTTTGCTCACATGTTCTTTCCTGCGTTATCCCCTGATTCTGTGGA

TAACCGTATTACCGCCTTTGAGTGAGCTGATACCGCTCGCCGCAGCCGAA

CGACCGAGCGCAGCGAGTCAGTGAGCGAGGAAGCGGAAGAGCGCCCAATA

CGCAAACCGCCTCTCCCCGCGCGTTGGCCGATTCATTAATGCAGCAGCTG

CGCGCTCGCTCGCTCACTGAGGCCGCCCGGGCAAAGCCCGGGCGTCGGGC

GACCTTTGGTCGCCCGGCCTCAGTGAGCGAGCGAGCGCGCAGAGAGGGAG

TGGCCAACTCCATCACTAGGGGTTCCTTGTAGTTAATGATTAACCCGCCA

TGCTACTTATCTACGTAGCCATGCTCTAGGACATTGATTATTGACTAGTG

GAGTTCCGCGTTACATAACTTACGGTAAATGGCCCGCCTGGCTGACCGCC

CAACGACCCCCGCCCATTGACGTCAATAATGACGTATGTTCCCATAGTAA

CGCCAATAGGGACTTTCCATTGACGTCAATGGGTGGAGTATTTACGGTAA

ACTGCCCACTTGGCAGTACATCAAGTGTATCATATGCCAAGTACGCCCCC

TATTGACGTCAATGACGGTAAATGGCCCGCCTGGCATTATGCCCAGTACA

TGACCTTATGGGACTTTCCTACTTGGCAGTACATCTACGTATTAGTCATC

GCTATTACCATGGTCGAGGTGAGCCCCACGTTCTGCTTCACTCTCCCCAT

CTCCCCCCCCTCCCCACCCCCAATTTTGTATTTATTTATTTTTTAATTAT

TTTGTGCAGCGATGGGGGCGGGGGGGGGGGGGGCGCGCGCCAGGCGGGG

CGGGGCGGGGCGAGGGGCGGGGCGGGGCGAGGCGGAGAGGTGCGGCGGCA

GCCAATCAGAGCGGCGCGCTCCGAAAGTTTCCTTTTATGGCGAGGCGGCG

GCGGCGGCGGCCCTATAAAAAGCGAAGCGCGCGGCGGGCGGGAGTCGCTG

CGCGCTGCCTTCGCCCCGTGCCCCGCTCCGCCGCCGCCTCGCGCCGCCCG

CCCCGGCTCTGACTGACCGCGTTACTAAAACAGGTAAGTCCGGCCTCCGC

GCCGGGTTTTGGCGCCTCCCGCGGGCGCCCCCCTCCTCACGGCGAGCGCT

GCCACGTCAGACGAAGGGCGCAGCGAGCGTCCTGATCCTTCCGCCCGGAC

GCTCAGGACAGCGGCCCGCTGCTCATAAGACTCGGCCTTAGAACCCCAGT

ATCAGCAGAAGGACATTTTAGGACGGGACTTGGGTGACTCTAGGGCACTG

GTTTTCTTTCCAGAGAGCGGAACAGGCGAGGAAAAGTAGTCCCTTCTCGG

CGATTCTGCGGAGGGATCTCCGTGGGGCGGTGAACGCCGATGATGCCTCT

-continued

ACTAACCATGTTCATGTTTTCTTTTTTTTTCTACAGGTCCTGGGTGACGA

ACAGGGTACC 3'

SEQ ID NO. 2
(miRNA expression cassette No. 2 - CXCR4):
5' GCCACCATGGCCACCGGCTCTCGCACAAGCCTGCTGCTGGCTTTCGG

ACTGCTGTGCCTGCCTTGGCTCCAGGAGGGCTCCGCCGCTAGCATCGATA

CCGTCGCTATGTGCTGGAGGCTTGCTGAAGGCTGTATGCTGTATTTATCG

GTATCATGCTGCGCGTTTTGGCCTCTGACTGACGCGCAGCATGACCGATA

AATACAGGACACAAGGCCTGTTACTAGCACTCACATGGAACAAATGGCCT

CTAGCCTGGAGGCTTGCTGAAGGCTGTATGCTGAAATCACATGCATACCG

CTTTGCGTTTTGGCCTCTGACTGACGCAAAGCGGTGCATGTGATTTCAGG

ACACAAGGCCTGTTACTAGCACTCACATGGAACAAATGGCCTCTAGCCTG

GAGGCTTGCTGAAGGCTGTATGCTGATATAATACGGAACAGCCAGCACGT

TTTGGCCTCTGACTGACGTGCTGGCTGCCGTATTATATCAGGACACAAGG

CCTGTTACTAGCACTCACATGGAACAAATGGCCTC 3'

SEQ ID NO: 3 = SEQ ID NO: 1 + SEQ ID NO: 2
5' TCTAGAATAATCAACCTCTGGATTACAAAATTTGTGAAAGATTGACT

GGTATTCTTAACTATGTTGCTCCTTTTACGCTATGTGGATACGCTGCTTT

AATGCCTTTGTATCATGCTATTGCTTCCCGTATGGCTTTCATTTTCTCCT

CCTTGTATAAATCCTGGTTGCTGTCTCTTTATGAGGAGTTGTGGCCCGTT

GTCAGGCAACGTGGCGTGGTGTGCACTGTGTTTGCTGACGCAACCCCCAC

TGGTTGGGGCATTGCCACCACCTGTCAGCTCCTTTCCGGGACTTTCGCTT

TCCCCCTCCCTATTGCCACGGCGGAACTCATCGCCGCCTGCCTTGCCCGC

TGCTGGACAGGGGCTCGGCTGTTGGGCACTGACAATTCCGTGGTGTTGTC

GGGGAAATCATCGTCCTTTCCTTGGCTGCTCGCCTGTGTTGCCACCTGGA

TTCTGCGCGGGACGTCCTTCTGCTACGTCCCTTCGGCCCTCAATCCAGCG

GACCTTCCTTCCCGCGGCCTGCTGCCGGCTCTGCGGCCTCTTCCGCGTCT

TCGCCTTCGCCCTCAGACGAGTCGGATCTCCCTTTGGGCCGCCTCCCCGC

CTAAGCTTATCGATACCGTCGAGATCTAACTTGTTTATTGCAGCTTATAA

TGGTTACAAATAAAGCAATAGCATCACAAATTTCACAAATAAAGCATTTT

TTTCACTGCATTCTAGTTGTGGTTTGTCCAAACTCATCAATGTATCTTAT

CATGTCTGGATCTCGACCTCGACTAGAGCATGGCTACGTAGATAAGTAGC

ATGGCGGGTTAATCATTAACTACAAGGAACCCCTAGTGATGGAGTTGGCC

ACTCCCTCTCTGCGCGCTCGCTCGCTCACTGAGGCCGGGCGACCAAAGGT

CGCCCGACGCCCGGGCTTTGCCCGGGCGGCCTCAGTGAGCGAGCGAGCGC

GCAGCTGGCGTAATAGCGAAGAGGCCCGCACCGATCGCCCTTCCCAACAG

TTGCGCAGCCTGAATGGCGAATGGCGATTCCGTTGCAATGGCTGGCGGTA

ATATTGTTCTGGATATTACCAGCAAGGCCGATAGTTTGAGTTCTTCTACT

CAGGCAAGTGATGTTATTACTAATCAAAGAAGTATTGCGACAACGGTTAA

TTTGCGTGATGGACAGACTCTTTTTACTCGGTGGCCTCACTGATTATAAAA

ACACTTCTCAGGATTCTGGCGTACCGTTCCTGTCTAAAATCCCTTTAATC

GGCCTCCTGTTTAGCTCCCGCTCTGATTCTAACGAGGAAAGCACGTTATA

-continued

CGTGCTCGTCAAAGCAACCATAGTACGCGCCCTGTAGCGGCGCATTAAGC

GCGGCGGGTGTGGTGGTTACGCGCAGCGTGACCGCTACACTTGCCAGCGC

CCTAGCGCCCGCTCCTTTCGCTTTCTTCCCTTCCTTTCTCGCCACGTTCG

CCGGCTTTCCCCGTCAAGCTCTAAATCGGGGGCTCCCTTTAGGGTTCCGA

TTTAGTGCTTTACGGCACCTCGACCCCAAAAAACTTGATTAGGGTGATGG

TTCACGTAGTGGGCCATCGCCCTGATAGACGGTTTTTCGCCCTTTGACGT

TGGAGTCCACGTTCTTTAATAGTGGACTCTTGTTCCAAACTGGAACAACA

CTCAACCCTATCTCGGTCTATTCTTTTGATTTATAAGGGATTTTGCCGAT

TTCGGCCTATTGGTTAAAAAATGAGCTGATTTAACAAAAATTTAACGCGA

ATTTTAACAAAATATTAACGTTTACAATTTAAATATTTGCTTATACAATC

TTCCTGTTTTTGGGGCTTTTCTGATTATCAACCGGGGTACATATGATTGA

CATGCTAGTTTTACGATTACCGTTCATCGATTCTCTTGTTTGCTCCAGAC

TCTCAGGCAATGACCTGATAGCCTTTGTAGAGACCTCTCAAAAATAGCTA

CCCTCTCCGGCATGAATTTATCAGCTAGAACGGTTGAATATCATATTGAT

GGTGATTTGACTGTCTCCGGCCTTTCTCACCCGTTTGAATCTTTACCTAC

ACATTACTCAGGCATTGCATTTAAAATATATGAGGGTTCTAAAAATTTTT

ATCCTTGCGTTGAAATAAAGGCTTCTCCCGCAAAAGTATTACAGGGTCAT

AATGTTTTTGGTACAACCGATTTAGCTTTATGCTCTGAGGCTTTATTGCT

TAATTTTGCTAATTCTTTGCCTTGCCTGTATGATTTATTGGATGTTGGAA

TTCCTGATGCGGTATTTTCTCCTTACGCATCTGTGCGGTATTTCACACCG

CATATGGTGCACTCTCAGTACAATCTGCTCTGATGCCGCATAGTTAAGCC

AGCCCCGACACCCGCCAACACCCGCTGACGCGCCCTGACGGGCTTGTCTG

CTCCCGGCATCCGCTTACAGACAAGCTGTGACCGTCTCCGGGAGCTGCAT

GTGTCAGAGGTTTTCACCGTCATCACCGAAACGCGCGAGACGAAAGGGCC

TCGTGATACGCCTATTTTTATAGGTTAATGTCATGATAATAATGGTTTCT

TAGACGTCAGGTGGCACTTTTCGGGGAAATGTGCGCGGAACCCCTATTTG

TTTATTTTTCTAAATACATTCAAATATGTATCCGCTCATGAGACAATAAC

CCTGATAAATGCTTCAATAATATTGAAAAAGGAAGAGTATGAGTATTCAA

CATTTCCGTGTCGCCCTTATTCCCTTTTTTGCGGCATTTTGCCTTCCTGT

TTTTGCTCACCCAGAAACGCTGGTGAAAGTAAAAGATGCTGAAGATCAGT

TGGGTGCACGAGTGGGTTACATCGAACTGGATCTCAACAGCGGTAAGATC

CTTGAGAGTTTTCGCCCCGAAGAACGTTTTCCAATGATGAGCACTTTTAA

AGTTCTGCTATGTGGCGCGGTATTATCCCGTATTGACGCCGGGCAAGAGC

AACTCGGTCGCCGCATACACTATTCTCAGAATGACTTGGTTGAGTACTCA

CCAGTCACAGAAAAGCATCTTACGGATGGCATGACAGTAAGAGAATTATG

CAGTGCTGCCATAACCATGAGTGATAACACTGCGGCCAACTTACTTCTGA

CAACGATCGGAGGACCGAAGGAGCTAACCGCTTTTTTGCACAACATGGGG

GATCATGTAACTCGCCTTGATCGTTGGGAACCGGAGCTGAATGAAGCCAT

ACCAAACGACGAGCGTGACACCACGATGCCTGTAGCAATGGCAACAACGT

TGCGCAAACTATTAACTGGCGAACTACTTACTCTAGCTTCCCGGCAACAA

-continued

```
TTAATAGACTGGATGGAGGCGGATAAAGTTGCAGGACCACTTCTGCGCTC

GGCCCTTCCGGCTGGCTGGTTTATTGCTGATAAATCTGGAGCCGGTGAGC

GTGGGTCTCGCGGTATCATTGCAGCACTGGGGCCAGATGGTAAGCCCTCC

CGTATCGTAGTTATCTACACGACGGGGAGTCAGGCAACTATGGATGAACG

AAATAGACAGATCGCTGAGATAGGTGCCTCACTGATTAAGCATTGGTAAC

TGTCAGACCAAGTTTACTCATATATACTTTAGATTGATTTAAAACTTCAT

TTTTAATTTAAAAGGATCTAGGTGAAGATCCTTTTTGATAATCTCATGAC

CAAAATCCCTTAACGTGAGTTTTCGTTCCACTGAGCGTCAGACCCCGTAG

AAAAGATCAAAGGATCTTCTTGAGATCCTTTTTTTCTGCGCGTAATCTGC

TGCTTGCAAACAAAAAAACCACCGCTACCAGCGGTGGTTTGTTTGCCGGA

TCAAGAGCTACCAACTCTTTTTCCGAAGGTAACTGGCTTCAGCAGAGCGC

AGATACCAAATACTGTCCTTCTAGTGTAGCCGTAGTTAGGCCACCACTTC

AAGAACTCTGTAGCACCGCCTACATACCTCGCTCTGCTAATCCTGTTACC

AGTGGCTGCTGCCAGTGGCGATAAGTCGTGTCTTACCGGGTTGGACTCAA

GACGATAGTTACCGGATAAGGCGCAGCGGTCGGGCTGAACGGGGGGTTCG

TGCACACAGCCCAGCTTGGAGCGAACGACCTACACCGAACTGAGATACCT

ACAGCGTGAGCTATGAGAAAGCGCCACGCTTCCCGAAGGGAGAAAGGCGG

ACAGGTATCCGGTAAGCGGCAGGGTCGGAACAGGAGAGCGCACGAGGGAG

CTTCCAGGGGGAAACGCCTGGTATCTTTATAGTCCTGTCGGGTTTCGCCA

CCTCTGACTTGAGCGTCGATTTTTGTGATGCTCGTCAGGGGGCGGAGCC

TATGGAAAAACGCCAGCAACGCGGCCTTTTTACGGTTCCTGGCCTTTTGC

TGGCCTTTTGCTCACATGTTCTTTCCTGCGTTATCCCCTGATTCTGTGGA

TAACCGTATTACCGCCTTTGAGTGAGCTGATACCGCTCGCCGCAGCCGAA

CGACCGAGCGCAGCGAGTCAGTGAGCGAGGAAGCGGAAGAGCGCCCAATA

CGCAAACCGCCTCTCCCCGCGCGTTGGCCGATTCATTAATGCAGCAGCTG

CGCGCTCGCTCGCTCACTGAGGCCGCCCGGGCAAAGCCCGGGCGTCGGGC

GACCTTTGGTCGCCCGGCCTCAGTGAGCGAGCGAGCGCGCAGAGAGGGAG

TGGCCAACTCCATCACTAGGGGTTCCTTGTAGTTAATGATTAACCCGCCA

TGCTACTTATCTACGTAGCCATGCTCTAGGACATTGATTATTGACTAGTG

GAGTTCCGCGTTACATAACTTACGGTAAATGGCCCGCCTGGCTGACCGCC

CAACGACCCCCGCCCATTGACGTCAATAATGACGTATGTTCCCATAGTAA

CGCCAATAGGGACTTTCCATTGACGTCAATGGGTGGAGTATTTACGGTAA

ACTGCCCACTTGGCAGTACATCAAGTGTATCATATGCCAAGTACGCCCCC

TATTGACGTCAATGACGGTAAATGGCCCGCCTGGCATTATGCCCAGTACA

TGACCTTATGGGACTTTCCTACTTGGCAGTACATCTACGTATTAGTCATC

GCTATTACCATGGTCGAGGTGAGCCCCACGTTCTGCTTCACTCTCCCCAT

CTCCCCCCCCTCCCCACCCCCAATTTTGTATTTATTTATTTTTTAATTAT

TTTGTGCAGCGATGGGGGGGGGGGGGGGGGGGGCGCGCGCCAGGCGGGGC

GGGGCGGGGCGAGGGGCGGGGCGGGGCGAGGCGGAGAGGTGCGGCGGCAG

CCAATCAGAGCGGCGCGCTCCGAAAGTTTCCTTTTATGGCGAGGCGGCGG

CGGCGGCGGCCCTATAAAAAGCGAAGCGCGCGGCGGGCGGGAGTCGCTGC
```

-continued

```
GCGCTGCCTTCGCCCCGTGCCCCGCTCCGCCGCCGCCTCGCGCCGCCCGC

CCCGGCTCTGACTGACCGCGTTACTAAAACAGGTAAGTCCGGCCTCCGCG

CCGGGTTTTGGCGCCTCCCGCGGGCGCCCCCCTCCTCACGGCGAGCGCTG

CCACGTCAGACGAAGGGCGCAGCGAGCGTCCTGATCCTTCCGCCCGGACG

CTCAGGACAGCGGCCCGCTGCTCATAAGACTCGGCCTTAGAACCCCAGTA

TCAGCAGAAGGACATTTTAGGACGGGACTTGGGTGACTCTAGGGCACTGG

TTTTCTTTCCAGAGAGCGGAACAGGCGAGGAAAAGTAGTCCCTTCTCGGC

GATTCTGCGGAGGGATCTCCGTGGGGCGGTGAACGCCGATGATGCCTCTA

CTAACCATGTTCATGTTTTCTTTTTTTTTCTACAGGTCCTGGGTGACGAA

CAGGGTACCGCCACCATGGCCACCGGCTCTCGCACAAGCCTGCTGCTGGC

TTTCGGACTGCTGTGCCTGCCTTGGCTCCAGGAGGGCTCCGCCGCTAGCA

TCGATACCGTCGCTATGTGCTGGAGGCTTGCTGAAGGCTGTATGCTGTAT

TTATCGGTATCATGCTGCGCGTTTTGGCCTCTGACTGACGCGCAGCATGA

CCGATAAATACAGGACACAAGGCCTGTTACTAGCACTCACATGGAACAAA

TGGCCTCTAGCCTGGAGGCTTGCTGAAGGCTGTATGCTGAAATCACATGC

ATACCGCTTTGCGTTTTGGCCTCTGACTGACGCAAAGCGGTGCATGTGAT

TTCAGGACACAAGGCCTGTTACTAGCACTCACATGGAACAAATGGCCTCT

AGCCTGGAGGCTTGCTGAAGGCTGTATGCTGATATAATACGGAACAGCCA

GCACGTTTTGGCCTCTGACTGACGTGCTGGCTGCCGTATTATATCAGGAC

ACAAGGCCTGTTACTAGCACTCACATGGAACAAATGGCCTC  3'
```

As will be appreciated by those skilled in the art, because the recombinant plasmid is a circular vector, the one or more sequences of the miRNA expression cassettes may be connected at the 3' end of SEQ ID NO. 1, as shown in SEQ ID NO. 3, or at the 5' end of SEQ ID NO. 1.

As will be appreciated by those skilled in the art, a perfect match of nucleotides with each of the miRNA expression cassette sequences is not necessary in order to have the desired result of decreased bioavailability of the target biomolecule as a result of the target cell producing the miRNA sequence that will bind to and degrade the mRNA of the target biomolecule. In some embodiments of the present disclosure, about 80% to about 100% nucleotide sequence matching with each of the miRNA expression cassettes causes the desired result. In some embodiments of the present disclosure, about 85% to about 100% nucleotide sequence matching with each of the miRNA expression cassettes causes the desired result. In some embodiments of the present disclosure, about 90% to about 100% nucleotide sequence matching with each of the miRNA expression cassettes causes the desired result. In some embodiments of the present disclosure, about 95% to about 100% nucleotide sequence matching with each of the miRNA expression cassettes causes the desired result.

Example 1—Expression Cassette

Expression cassettes for expressing miRNA were synthesized. The synthesized miRNA expression cassettes were cloned into the pAVA-00200 plasmid backbone containing the CASI promoter, multiple cloning site (MCS), Woodchuck Hepatitis Virus post-transcriptional regulatory element (WPRE), and Simian virus 40 (SV40) polyadenylation (polyA) sequence, all flanked by the AAV2 inverted terminal repeats (ITR). pAVA-00200 was cut with the restriction enzymes KpnI and XbaI in the MCS and separated on a 1% agarose gel. The band of interest was excised and purified using a gel extraction kit. Each miRNA expression cassette was amplified by polymerase chain reaction (PCR) using Taq polymerase and the PCR products were gel purified and the bands on interest were also excised and purified using a gel extraction kit. These PCR products contained the miRNA expression cassettes in addition to 15 base pair 5' and 3' overhangs that aligned with the ends of the linearized pAVA-00200 backbone. Using in-fusion cloning, the amplified miRNA expression cassettes are integrated with the pAVA-00200 backbone via homologous recombination. The resulting RP contained the following: 5' ITR, CASI promoter, miRNA expression cassette, WPRE, SV40 polyA and ITR 3'.

The invention claimed is:

1. A composition that comprises a recombinant plasmid (RP) comprising a sequence of nucleotides that is SEQ ID NO: 2.

2. The composition of claim 1, wherein the RP is encapsulated in a protein coat, a lipid vesicle, or any combination thereof.

* * * * *

SEQUENCE LISTING

```
Sequence total quantity: 3
SEQ ID NO: 1          moltype = DNA  length = 5807
FEATURE               Location/Qualifiers
source                1..5807
                      mol_type = other DNA
                      organism = synthetic construct
SEQUENCE: 1
tctagaataa tcaacctctg gattacaaaa tttgtgaaag attgactggt attcttaact  60
atgttgctcc ttttacgcta tgtggatacg ctgctttaat gcctttgtat catgctattg  120
cttcccgtat ggctttcatt ttctcctcct tgtataaatc ctggttgctg tctctttatg  180
aggagttgtg gcccgttgtc aggcaacgtg gcgtggtgtg cactgtgttt gctgacgcaa  240
cccccactgg ttggggcatt gccaccacct gtcagctcct ttccgggact ttcgctttcc  300
ccctccctat tgccacggcg gaactcatcg ccgcctgcct tgcccgctgc tggacagggg  360
ctcggctgtt gggcactgac aattccgtgg tgttgtcgga gaaatcatcg tcctttcctt  420
ggctgctcgc ctgtgttgcc acctggattc tgcgcgggac gtccttctgc tacgtccctt  480
cggccctcaa tccagcggac cttccttccc gcggcctgct gccggctctg cggcctcttc  540
cgcgtcttcg ccttcgccct cagacgagtc ggatctccct ttgggccgcc tccccgccta  600
agcttatcga taccgtcgag atctaacttg tttattgcag cttataatgg ttacaaataa  660
agcaatagca tcacaaattt cacaaataaa gcattttttt cactgcattc tagttgtggt  720
ttgtccaaac tcatcaatgt atcttatcat gtctggatct cgacctcgac tagagcatgg  780
ctacgtagat aagtagcatg gcgggttaat cattaactac aaggaacccc tagtgatgga  840
gttggccact ccctctctgc gcgctcgctc gctcactgag gccgggcgac caaaggtcgc  900
ccgacgcccg ggctttgccc gggcggcctc agtgagcgag cgagcgcgca gctggcgtaa  960
tagcgaagag gcccgcaccg atcgcccttc ccaacagttg cgcagcctga atggcgaatg  1020
gcgattccgt tgcaatggct ggcggtaata ttgttctgga tattaccagc aaggccgata  1080
gtttgattc ttctactcag gcaagtgatg ttattactaa tcaaagaagt attgcgacaa  1140
cggttaattt gcgtgatgga cagactcttt tactcggtgg cctcactgat tataaaaaca  1200
cttctcagga ttctggcgta ccgttcctgt ctaaaatccc tttaatcggc ctcctgttta  1260
gctcccgctc tgattctaac gaggaaagca cgttatacgt gctcgtcaaa gcaaccatag  1320
tacgcgccct gtagcggcgc attaagcgcg gcgggtgtgg tggttacgcg cagcgtgacc  1380
gctacacttg ccagcgccct agcgcccgct cctttcgctt tcttcccttc ctttctcgcc  1440
acgttcgccg gctttccccg tcaagctcta aatcgggggc tccctttagg gttccgattt  1500
agtgctttac ggcacctcga ccccaaaaaa cttgattagg gtgatggttc acgtagtggg  1560
ccatcgccct gatagacggt ttttcgccct ttgacgttgg agtccacgtt ctttaatagt  1620
ggactcttgt tccaaactgg aacaacactc aaccctatct cggtctattc ttttgattta  1680
taagggattt tgccgatttc ggcctattgg ttaaaaaatg agctgattta acaaaaattt  1740
aacgcgaatt ttaacaaaat attaacgttt acaatttaaa tatttgctta tacaatcttc  1800
ctgttttttg ggcttttctg attatcaacc ggggtacata tgattgacat gctagtttta  1860
cgattaccgt tcatcgattc tcttgtttgc tccagatct caggcaatga cctgatagcc  1920
tttgtagaga cctctcaaaa atagctaccc tctccggcat gaatttatca gctagaacgg  1980
ttgaatatca tattgatggt gatttgactg tctccggcct ttctcacccg tttgaatctt  2040
tacctacaca ttactcaggc attgcattta aaatatatga gggttctaaa aatttttatc  2100
cttgcgttga aataaaggct tctccccgca aagtattaca gggtcataat gtttttggta  2160
caaccgattt agctttatgc tctgaggctt tattgcttaa ttttgctaat tctttgcctt  2220
gcctgtatga tttattggat gttggaattc ctgatgcggt attttctcct tacgcatctg  2280
tgcggtattt cacaccgcat atggtgcact ctcagtacaa tctgctctga tgccgcatag  2340
ttaagccagc cccgacaccc gccaacaccc gctgacgcgc cctgacgggc ttgtctgctc  2400
ccggcatccg cttacagaca agctgtgacc gtctccggga gctgcatgtg tcagaggttt  2460
tcaccgtcat caccgaaacg cgcgagacga aagggcctcg tgatacgcct attttttatag  2520
gttaatgtca tgataataat ggtttcttag acgtcaggtg gcacttttcg gggaaatgtg  2580
cgcggaaccc ctatttgttt attttttctaa atacattcaa atatgtatcc gctcatgaga  2640
caataaccct gataaatgct tcaataatat tgaaaaagga agagtatgag tattcaacat  2700
ttccgtgtcg cccttattcc cttttttgcg gcattttgcc ttcctgtttt tgctcaccca  2760
gaaacgctgg tgaaagtaaa agatgctgaa gatcagttgg gtgcacgagt gggttacatc  2820
gaactggatc tcaacagcgg taagatcctt gagagttttc gccccgaaga acgttttcca  2880
atgatgagca cttttaaagt tctgctatgt ggcgcggtat tatcccgtat tgacgccggg  2940
caagagcaac tcggtcgccg catacactat tctcagaatg acttggttga gtactcacca  3000
gtcacagaaa agcatcttac ggatggcatg acagtaagag aattatgcag tgctgccata  3060
accatgagt ataacactgc ggccaactta cttctgacaa cgatcggagg accgaaggag  3120
ctaaccgctt ttttgcacaa catgggggat catgtaactc gccttgatcg ttgggaaccg  3180
gagctgaatg aagccatacc aaacgacgag cgtgacacca cgatgcctgt agcaatggca  3240
acaacgttgc gcaaactatt aactggcgaa ctacttactc tagcttcccg gcaacaatta  3300
atagactgga tggaggcgga taaagttgca ggaccacttc tgcgctcggc ccttccggct  3360
ggctggttta ttgctgataa atctggagcc ggtgagcgtg ggtctcgcgg tatcattgca  3420
gcactggggc cagatggtaa gccctcccgt atcgtagtta tctacacgac ggggagtcag  3480
gcaactatgg atgaacgaaa tagacagatc gctgagatag gtgcctcact gattaagcat  3540
```

-continued

```
tggtaactgt cagaccaagt ttactcatat atactttaga ttgatttaaa acttcatttt    3600
taatttaaaa ggatctaggt gaagatcctt tttgataatc tcatgaccaa aatcccttaa    3660
cgtgagtttt cgttccactg agcgtcagac cccgtagaaa agatcaaagg atcttcttga    3720
gatccttttt ttctgcgcgt aatctgctgc ttgcaaacaa aaaaaccacc gctaccagcg    3780
gtggtttgtt tgccggatca agagctacca actctttttc cgaaggtaac tggcttcagc    3840
agagcgcaga taccaaatac tgtccttcta gtgtagccgt agttaggcca ccacttcaag    3900
aactctgtag caccgcctac atacctcgct ctgctaatcc tgttaccagt ggctgctgcc    3960
agtggcgata agtcgtgtct taccgggttg gactcaagac gatagttacc ggataaggcg    4020
cagcggtcgg gctgaacggg gggttcgtgc acacagccca gcttggagcg aacgacctac    4080
accgaactga gatacctaca gcgtgagcta tgagaaagcg ccacgcttcc cgaagggaga    4140
aaggcggaca ggtatccggt aagcggcagg gtcggaacag gagagcgcac gagggagctt    4200
ccagggggaa acgcctggta tctttatagt cctgtcgggt ttcgccacct ctgacttgag    4260
cgtcgatttt tgtgatgctc gtcagggggg cggagcctat ggaaaaacgc cagcaacgcg    4320
gcctttttac ggttcctggc cttttgctgg ccttttgctc acatgttctt tcctgcgtta    4380
tcccctgatt ctgtggataa ccgtattacc gcctttgagt gagctgatac cgctcgccgc    4440
agccgaacga ccgagcgcag cgagtcagtg agcgaggaag cggaagagcg cccaatacgc    4500
aaaccgcctc tccccgcgcg ttggccgatt cattaatgca gcagctgcgc gctcgctcgc    4560
tcactgaggc cgcccgggca aagcccgggc gtcgggcgac ctttggtcgc ccggcctcag    4620
tgagcgagcg agcgcgcaga gagggagtgg ccaactccat cactagggGt tccttgtagt    4680
taatgattaa cccgccatgc tacttatcta cgtagccatg ctctaggaca ttgattattg    4740
actagtggag ttccgcgtta cataacttac ggtaaatggc ccgcctggct gaccgcccaa    4800
cgacccccgc ccattgacgt caataatgac gtatgttccc atagtaacgc caatagggac    4860
tttccattga cgtcaatggg tggagtattt acggtaaact gcccacttgg cagtacatca    4920
agtgtatcat atgccaagta cgccccctat tgacgtcaat gacggtaaat ggcccgcctg    4980
gcattatgcc cagtacatga ccttatggga ctttcctact tggcagtaca tctacgtatt    5040
agtcatcgct attaccatgg tcgaggtgag ccccacgttc tgcttcactc tccccatctc    5100
cccccctcc ccaccccaa tttttgtattt atttattttt taattatttt gtgcagcgat     5160
ggggggcgggg ggggggggggg gcgcgcgcca ggcggggcgg ggcggggcga ggggcgggggc  5220
ggggcgaggc ggagaggtgc ggcggcagcc aatcagagcg gcgcgctccg aaagtttcct    5280
tttatggcga ggcggcggcg gcggcggccc tataaaaagc gaagcgcgcg gcgggcgggga   5340
gtcgctgcgc gctgccttcg ccccgtgccc cgctccgccg ccgcctcgcg ccgcccgccc    5400
cggctctgac tgaccgcgtt actaaaacag gtaagtccgg cctccgcgcc gggttttggc    5460
gcctcccgcg ggcgcccccc tcctcacggc gagcgctgcc acgtcagacg aagggcgcag    5520
cgagcgtcct gatccttccg cccggacgct caggacagcg gcccgctgct cataagactc    5580
ggccttagaa ccccagtatc agcagaagga cattttaggg cgggacttgg gtgactctag    5640
ggcactggtt ttctttccag agagcggaac aggcgaggaa aagtagtccc ttctcggcga    5700
ttctgcggag ggatctccgt ggggcggtga acgccgatga tgcctctact aaccatgttc    5760
atgttttctt ttttttttcta caggtcctgg gtgacgaaca gggtacc                 5807
```

```
SEQ ID NO: 2           moltype = DNA   length = 532
FEATURE                Location/Qualifiers
source                 1..532
                       mol_type = other DNA
                       organism = synthetic construct
SEQUENCE: 2
gccaccatgg ccaccggctc tcgcacaagc ctgctgctgg ctttcggact gctgtgcctg    60
ccttgctcc aggagggctc cgccgctagc atcgataccg tcgctatgtg ctggaggctt      120
gctgaaggct gtatgctgta tttatcggta tcatgctgcg cgttttggcc tctgactgac     180
gcgcagcatg accgataaat acaggacaca aggcctgtta ctagcactca catggaacaa     240
atggcctcta gcctggaggc ttgctgaagg ctgtatgctg aaatcacatg cataccgctt     300
tgcgttttgg cctctgactg acgcaaagcg gtgcatgtga tttcaggaca caaggcctgt     360
tactagcact cacatggaac aaatggcctc tagcctggag gcttgctgaa ggctgtatgc     420
tgatataata cggaacagcc agcacgtttt ggcctctgac tgacgtgctg gctgccgtat     480
tatatcagga cacaaggcct gttactagca ctcacatgga caaatggcc tc             532
```

```
SEQ ID NO: 3           moltype = DNA   length = 6339
FEATURE                Location/Qualifiers
source                 1..6339
                       mol_type = other DNA
                       organism = synthetic construct
SEQUENCE: 3
tctagaataa tcaacctctg gattacaaaa tttgtgaaag attgactggt attcttaact     60
atgttgctcc ttttacgcta tgtggatacg ctgctttaat gcctttgtat catgctattg     120
cttcccgtat ggctttcatt ttctcctcct tgtataaatc ctggttgctg tctctttatg     180
aggagttgtg gcccgttgtc aggcaacgtg gcgtggtgtg cactgtgttt gctgacgcaa     240
cccccactg ttggggcatt gccaccacct gtcagctcct ttccgggact ttcgctttcc      300
ccctccctat tgccacggcg gaactcatcg ccgcctgcct tgcccgctgc tggacagggg     360
ctcggctgtt gggcactgac aattccgtgg tgttgtcggg gaaatcatcg tcctttcctt     420
ggctgctcgc ctgtgttgcc acctggattc tgcgcgggac gtccttctgc tacgtccctt     480
cggccctcaa tccagcggac cttccttccc gcggcctgct gccggctctg cggcctcttc     540
cgcgtcttcg ccttcgccct cagacgagtc ggatctccct ttgggccgcc tccccgccta     600
agcttatcga taccgtcgag atctaacttg tttattgcag cttataatgg ttacaaataa     660
agcaatagca tcacaaattt cacaaataaa gcattttttt cactgcattc tagttgtggt     720
ttgtccaaac tcatcaatgt atcttatcat gtctggatct cgacctcgac tagagtcatgg    780
ctacgtagat aagtagcatg gcgggttaat cattaactac aaggaacccc tagtgatgga     840
gttggccact ccctctctgc gcgctcgctc gctcactgag gccgggcgac caaaggtcgc     900
ccgacgcccg gctttgccc gggcggcctc agtgagcgag cgagcgcgca gctggcgtaa      960
tagcgaagag gcccgcaccg atcgcccttc ccaacagttg cgcagcctga atggcgaatg    1020
gcgattccgt tgcaatggct ggcggtaata ttgttctgga tattaccagc aaggccgata   1080
```

-continued

```
gtttgagttc ttctactcag gcaagtgatg ttattactaa tcaaagaagt attgcgacaa   1140
cggttaattt gcgtgatgga cagactcttt tactcggtgg cctcactgat tataaaaaca   1200
cttctcagga ttctggcgta ccgttcctgt ctaaaatccc tttaatcggc ctcctgttta   1260
gctcccgctc tgattctaac gaggaaaagca cgttatacgt gctcgtcaaa gcaaccatag   1320
tacgcgccct gtagcggcgc attaagcgcg gcgggtgtgg tggttacgcg cagcgtgacc   1380
gctacacttg ccagcgccct agcgcccgct cctttcgctt tcttcccttc ctttctcgcc   1440
acgttcgccg gctttccccg tcaagctcta aatcggggc tccctttagg gttccgattt   1500
agtgctttac ggcacctcga ccccaaaaaa cttgattagg gtgatggttc acgtagtggg   1560
ccatcgccct gatagacggt ttttcgccct ttgacgttgg agtccacgtt ctttaatagt   1620
ggactcttgt tccaaactgg aacaacactc aaccctatct cggtctattc ttttgattta   1680
taagggattt tgccgatttc ggcctattgg ttaaaaaatg agctgattta acaaaaattt   1740
aacgcgaatt ttaacaaaat attaacgttt acaatttaaa tatttgctta tacaatcttc   1800
ctgtttttgg ggcttttctg attatcaacc ggggtacata tgattgacat gctagtttta   1860
cgattaccgt tcatcgattc tcttgtttgc tccagactct caggcaatga cctgatagcc   1920
tttgtagaga cctctcaaaa atagctaccc tctccggcat gaatttatca gctagaacgg   1980
ttgaatatca tattgatggt gatttgactg tctccggcct ttctcacccg tttgaatctt   2040
tacctacaca ttactcaggc attgcattta aaatatatga gggttctaaa aatttttatc   2100
cttgcgttga aataaaggct tctcccgcaa aagtattaca gggtcataat gtttttggta   2160
caaccgattt agctttatgc tctgaggctt tattgcttaa ttttgctaat tctttgcctt   2220
gcctgtatga tttattggat gttggaattc ctgatgcggt attttctcct tacgcatctg   2280
tgcggtattt cacaccgcat atggtgcact ctcagtacaa tctgctctga tgccgcatag   2340
ttaagccagc cccgacaccc gccaacaccc gctgacgcgc cctgacgggc ttgtctgctc   2400
ccggcatccg cttacagaca agctgtgacc gtctccggga gctgcatgtg tcagaggttt   2460
tcaccgtcat caccgaaacg cgcgagacga aaggcctcg tgatacgcct attttttatag   2520
gttaatgtca tgataataat ggtttcttag acgtcaggtg gcacttttcg gggaaatgtg   2580
cgcggaaccc ctatttgttt atttttctaa atacattcaa atatgtatcc gctcatgaga   2640
caataacccl gataaatgct tcaataatat tgaaaaagga agagtatgag tattcaacat   2700
ttccgtgtcg cccttattcc cttttttgcg gcattttgcc ttcctgtttt tgctcaccca   2760
gaaacgctgg tgaaagtaaa agatgctgaa gatcagttgg gtgcacgagt gggttacatc   2820
gaactggatc tcaacagcgg taagatcctt gagagttttc gccccgaaga acgttttcca   2880
atgatgagca ctttttaaagt tctgctatgt ggcgcggtat tatcccgtat tgacgccggg   2940
caagagcaac tcggtcgccg catacactat tctcagaatg acttggttga gtactcacca   3000
gtcacagaaa agcatcttac ggatggcatg acagtaagag aattatgcag tgctgccata   3060
accatgagtg ataacactgc ggccaactta cttctgacaa cgatcggagg accgaaggag   3120
ctaaccgctt ttttgcacaa catgggggat catgtaactc gccttgatcg ttgggaaccg   3180
gagctgaatg aagccatacc aaacgacgag cgtgacacca cgatgcctgt agcaatggca   3240
acaacgttgc gcaaactatt aactggcgaa ctacttactc tagcttcccg gcaacaatta   3300
atagactgga tggaggcgga taaagttgca ggaccacttc tgcgctcggc ccttccggct   3360
ggctggttta ttgctgataa atctggagcc ggtgagcgtg ggtctcgcgg tatcattgca   3420
gcactgggc cagatggtaa gccctcccgt atcgtagtta tctacacgac ggggagtcag   3480
gcaactatgg atgaacgaaa tagacagatc gctgagatag gtgcctcact gattaagcat   3540
tggtaactgt cagaccaagt ttactcatat atactttaga ttgatttaaa acttcatttt   3600
taatttaaaa ggatctaggt gaagatcctt tttgataatc tcatgaccaa aatcccttaa   3660
cgtgagtttt cgttccactg agcgtcagac cccgtagaaa agatcaaagg atcttcttga   3720
gatccttttt ttctgcgcgt aatctgctgc ttgcaaacaa aaaaaccacc gctaccagcg   3780
gtggtttgtt tgccggatca agagctacca actcttttc cgaaggtaac tggcttcagc   3840
agagcgcaga taccaaatac tgtccttcta gtgtagccgt agttaggcca ccacttcaag   3900
aactctgtag caccgcctac atacctcgct ctgctaatcc tgttaccagt ggctgctgcc   3960
agtggcgata agtcgtgtct taccgggttg gactcaagac gatagttacc ggataaggcg   4020
cagcggtcgg gctgaacggg gggttcgtgc acacagccca gcttggagcg aacgacctac   4080
accgaactga gatacctaca gcgtgagcta tgagaaagcg ccacgcttcc cgaagggaga   4140
aaggcggaca ggtatccggt aagcggcagg gtcggaacag gagagcgcac gagggagctt   4200
ccagggggaa acgcctggta tctttatagt cctgtcgggt ttcgccacct ctgacttgag   4260
cgtcgatttt tgtgatgctc gtcaggggg cggagcctat ggaaaaacgc cagcaacgcg   4320
gcctttttac ggttcctggc cttttgctgg ccttttgctc acatgttctt tcctgcgtta   4380
tcccctgatt ctgtggataa ccgtattacc gcctttgagt gagctgatac cgctcgccgc   4440
agccgaacga ccgagcgcag cgagtcagtg agcgaggaag cggaagagcg cccaatacgc   4500
aaaccgcctc tccccgcgcg ttggccgatt cattaatgca gcagctgcgc gctcgctcgc   4560
tcactgaggc cgcccgggca aagcccgggc gtcgggcgac ctttggtcgc ccggcctcag   4620
tgagcgagcg agcgcgcaga gagggagtgg ccaactccat cactaggggt tccttgtagt   4680
taatgattaa cccgccatgc tacttatcta cgtagccatg ctctaggaca ttgattattg   4740
actagtggag ttccgcgtta cataacttac ggtaaatggc ccgcctggct gaccgcccaa   4800
cgacccccgc ccattgacgt caataatgac gtatgttccc atagtaacgc caatagggac   4860
tttccattga cgtcaatggg tggagtattt acggtaaact gcccacttgg cagtacatca   4920
agtgtatcat atgccaagta cgccccctat tgacgtcaat gacggtaaat ggcccgcctg   4980
gcattatgcc cagtacatga ccttatggga ctttcctact tggcagtaca tctacgtatt   5040
agtcatcgct attaccatgg tcgaggtgag ccccacgttc tgcttcactc tccccatctc   5100
cccccctcc ccaccccaa tttttgtattt atttattttt taattatttt gtgcagcgat   5160
ggggcgggg gggggggggg gcgcgcgcca ggcggggcgg ggcggggcga gggggcgggc   5220
gggcgaggc ggagaggtgc ggcggcagcc aatcagagcg gcgcgctccg aaagtttcct   5280
tttatgcgga ggcggcggcg gcggcggccc tataaaaagc gaagcgcgcg gcgggcggga   5340
gtcgctcgc gctgccttcg ccccgtgccc cgctccgccg ccgcctcgcg ccgcccgccc   5400
cggctctgac tgaccgcgtt actaaaacag gtaagtccgg cctccgcgcc gggttttggc   5460
gcctcccgcg ggcgcccccc tcctcacggc gagcgctgcc acgtcagacg aagggcgcag   5520
cgagcgtcct gatccttccg cccggacgct caggacagcg gcccgctgct cataagactc   5580
ggccttagaa ccccagtatc agcagaagga catttttagga cgggacttgg gtgactctag   5640
ggcactggtt ttctttccag agagcggaac aggcgaggaa aagtagtccc ttctcggcga   5700
ttctgcggag ggatctccgt ggggcggtga acgccgatga tgcctctact aaccatgttc   5760
atgtttttctt ttttttcta caggtcctgg gtgacgaaca gggtaccgcc accatggcca   5820
```

-continued

```
ccggctctcg cacaagcctg ctgctggctt tcggactgct gtgcctgcct tggctccagg   5880
agggctccgc cgctagcatc gataccgtcg ctatgtgctg gaggcttgct gaaggctgta   5940
tgctgtattt atcggtatca tgctgcgcgt tttggcctct gactgacgcg cagcatgacc   6000
gataaataca ggacacaagg cctgttacta gcactcacat ggaacaaatg gcctctagcc   6060
tggaggcttg ctgaaggctg tatgctgaaa tcacatgcat accgctttgc gttttggcct   6120
ctgactgacg caaagcggtg catgtgattt caggacacaa ggcctgttac tagcactcac   6180
atggaacaaa tggcctctag cctggaggct tgctgaaggc tgtatgctga tataatacgg   6240
aacagccagc acgttttggc ctctgactga cgtgctggct gccgtattat atcaggacac   6300
aaggcctgtt actagcactc acatggaaca aatggcctc                           6339
```